United States Patent [19]

Cook et al.

[11] Patent Number: 5,359,051
[45] Date of Patent: Oct. 25, 1994

[54] COMPOUNDS USEFUL IN THE SYNTHESIS OF NUCLEIC ACIDS CAPABLE OF CLEANING RNA

[75] Inventors: Phillip D. Cook; Charles J. Guinosso; Thomas Bruice, all of Carlsbad, Calif.

[73] Assignee: ISIS Pharmaceuticals, Carlsbad, Calif.

[21] Appl. No.: 846,556

[22] Filed: Mar. 5, 1992

Related U.S. Application Data

[63] and a continuation-in-part of Ser. No. 566,977, Aug. 13, 1990, abandoned.

[51] Int. Cl.$^5$ .......................................... C07H 19/207
[52] U.S. Cl. ............................. 536/26.7; 536/25.34; 536/24.5
[58] Field of Search ..................... 536/23.1, 24.3, 24.5

[56] References Cited

U.S. PATENT DOCUMENTS

| | | | |
|---|---|---|---|
| 4,814,438 | 3/1989 | Armour et al. ....................... | 536/23 |
| 4,816,569 | 3/1989 | Miyoshi ................................ | 536/29 |

OTHER PUBLICATIONS

Tramontano et al., "Chemical Reactivity at an Antibody Binding Site Elicited by Mechanistic Design of a Synthetic Antigen," *Proc. Nat. Acad. Sci. USA*, 83, 6736–6740 (1986).

Inouye, "Antisense RNA: Its Functions and Applications in Gene Regulation–A Review," *Gene*, 72, 25–34, (1988).

Van Der Krol et al., "Antisense Genes in Plants: An Overview," *Gene*, 72, 45–50 (1988).

Zuckerman et al., "A Hybrid Sequence-Selective Ribonuclease S," *J. Am. Chem. Soc.*, 110, 6592–6594 (1988).

Helene et al., "Control of Gene Expression by Oligodeoxynucleotides Covalently Linked to Intercalating Agents and Nucleic Acid Cleaving Reagents," Ch. 7 in *Oligodeoxynucleotides, Antisense Inhibitors of Gene Expression*, J. S. Cohen ed., CRC Press, Boca Raton, Fla., 1989, pp. 137–172.

Thuong et al., "Oligodeoxynucleotides Covalently Linked to Intercalating and Reactive Substances: Synthesis, Characterization and Physicochemical Studies," Ch. 2 in *Oligodeoxynucleotides. Antisense Inhibitors of Gene Expression*, J. S. Cohen ed., CRC Press, Boca Raton, Fla., 1989, pp. 24–51.

Knorre et al., "Oligonucleotides Linked to Reactive Groups," Ch. 8 in *Oligodeoxynucleotides. Antisense Inhibitors of Gene Expression*, J. S. Cohen ed., CRC Press, Boca Raton, Fla., 1989, pp. 173–196.

Akabori et al., "Synthese von Imidazolderivaten aus α-Aminosäuren. III. Synthese von Zwei Hoheren Homologen.des Histamins," *Bull. Chem. Soc. Japan*, 11, 208–213 (1936).

Rothenberg et al., "Oligodeoxynucleotides as Anti--Sense Inhibitors of Gene Expression: Therapeutic Implications," *J. Nat. Cancer Inst. USA*, 81(20), 1539–1544 (1989).

Kochetkov et al., *Organic Chemistry of Nucleic Acids, Part B*, Plenum Press, New York, 1972, pp. 488–490.

Offensperger et al., "In vivo Inhibition of Duck Hepatitis B Virus Replication and Gene Expression by Phosphorothioate Modified Antisense Oligodeoxynucleotides," *EMBO J.*, 12(3), 1257–1262 (1993).

Simons et al., "Antisense c-myb Oligonucleotides In-
(List continued on next page.)

Primary Examiner—Johnnie R. Brown
Assistant Examiner—L. Eric Crane
Attorney, Agent, or Firm—Woodcock Washburn Kurtz Mackiewicz & Norris

[57] ABSTRACT

Compositions and methods for modulating the activity of RNA are disclosed. In accordance with preferred embodiments, antisense compositions are prepared comprising targeting and reactive portions. In preferred embodiments, the reactive portions comprise one or two imidazole functionalities conjugated to the targeting oligonucleotide via linkers with and without intervening intercalating moieties and act through phosphorodiester hydrolytic bond cleavage. Therapeutics, diagnostics and research methods are also disclosed. Synthetic nucleosides and nucleoside fragments are also provided which are useful for elaboration of oligonucleotides for such purposes.

2 Claims, No Drawings

OTHER PUBLICATIONS hibit Intimal Arterial Smooth Muscle Cell Accumulation in vivo," *Nature*, 359, 67–70 (1992).

Burch et al., "Oligonucleotides Antisense of the Interleukin 1 Receptor mRNA Block the Effects of Interleukin 1 in Cultured Murine and Human Fibroblasts and in Mice," *J. Clinical Investigations*, 88, 1190–1196 (1991).

Kitajima et al., "Ablation of Transplanted HTLV–I Tax-Transformed Tumors in Mice by Antisense Inhibition of NF–kB," *Science*, 258, 1792–1795 (1992).

Higgins et al., "Antisense Inhibition of the p65 Subunit of NF–kB Blocks Tumorigenicity and Causes Tumor Regression," *Proc. Nat. Acad. Sci. USA*, 90, 9901–9905 (1993).

Vlassov, "Inhibition of Tick–Borne Viral Encephalitis Expression Using Covalently Linked Oligonucleotide Analogs," Abstract from program entitled *Oligodeoxynucleotides as Antisense Inhibitors of Gene Expression: Therapeutic Implications*, Natl. Cancer Inst. & Natl. Inst. of Allergy Infectious Dis. publ., Jun. 18–21, 1989, Rockville, Md.

C. A. Stein & J. S. Cohen, *Cancer Research*, vol. 48, pp. 2659–2668 (1988).

J. Walder, *Genes & Development*, vol. 2, pp. 502–504 (1988).

C. J. Marcus–Sekura, *Anal. Biochemistry*, vol. 172, 289–295 (1988).

G. Zon, *Journal of Protein Chemistry*, vol. 6, pp. 131–145 (1987).

G. Zon, *Pharmaceutical Research*, vol. 5, pp. 539–549 (1988).

A. R. Van der Krol, J. N. Mol. & A. R. Stuitje, *BioTechniques*, vol. 6, pp. 958–973 (1988).

D. S. Loose–Mitchell, *TIPS*, vol. 9, pp. 45–47 (1988).

Cazenave, N. Loreau, N. T. Thuong, J. J. Toulme and C. Helene in *Nucleic Acid Research*, vol. 15, pp. 4717–4736, (1987).

J. F. Constant, P. Laugaa, B. P. Roques & J. Lhomme, in *Biochemistry*, vol. 27, pp. 3997–4003 (1988).

A. T. Yeung, B. K. Jones and C. T. Chu in *Biochemistry*, vol. 27, pp. 2304–3210 (1988).

R. B. Meyer in the *Journal of American Chemical Society*, vol., 111, pp. 8517–8519 (1989).

D. G. Knorre an V. V. Vlassov, *Progress in Nucleic Acid Research and Molecular Biology*, vol. 32, pp. 291–320 (1985).

T. L. Doan, L. Perrouault, M. Chassignol, N. T. Thuong, & C. Helene, in *Nucleic Acids Research*, vol. 15, pp. 8643–8659 (1987).

D. S. Sigman, in *Accounts of Chemical Research*, vol. 19, pp. 180–186 (1986).

G. B. Dreyer and P. B. Dervan, in *Proceedings of the National Academy of Sciences*, U.S.A., vol. 82, pp. 968–972 (1985).

M. Caruthers, *Oligonucleotides. Antisense Inhibitors of Gene Expression.*, pp. 7–24, J. S. Cohen, ed. (CRC Press, Inc. Boca Raton, Fla., 1989).

*Journal of American Chemical Society*, vol. 112, pp. 1253–1255 (1990) or elemental sulfur, S. Beaucage et al., *Tetrahedron Letters*, vol. 22, pp. 1859–1862 (1981).

Spalholtz et al., *J. Virol.*, 61, 2128–2137 (1987).

COMPOUNDS USEFUL IN THE SYNTHESIS OF NUCLEIC ACIDS CAPABLE OF CLEANING RNA

RELATED APPLICATIONS

This application is a continuation-in-part of application Ser. No. US91/00243, filed Jan. 11, 1991, which is a continuation-in-part of application Ser. No. 463,358, filed Jan. 11, 1990 and application Ser. No. 566,977, filed Aug. 13, 1990 both now abandoned. These applications are assigned to the assignee of this invention. The entire disclosure of each is incorporated herein by reference.

FIELD OF THE INVENTION

This invention relates to materials and methods for detecting and modulating the activity of RNA. The invention generally relates to compounds which are capable of specific hybridization with a nucleotide sequence of an RNA. In accordance with preferred embodiments, this invention is directed to the design, synthesis, and application of oligonucleotides and to methods for assaying for RNA and for RNA products by hybridization with such RNA, diagnosing diseases, and cleaving RNA in a site specific fashion.

BACKGROUND OF THE INVENTION

It is well known that most of the bodily states in mammals, including most disease states, are effected by proteins. Such proteins, either acting directly or through their enzymatic or other functions, contribute in major proportion to many diseases in animals and man. Classical therapeutics has generally focused upon interactions with such proteins in efforts to moderate their disease-causing or disease-potentiating functions. Recently, however, attempts have been made to modulate the actual production of such proteins by interactions with the intracellular RNA molecules that code for their synthesis. By interfering with the production of proteins, it has been hoped to effect therapeutic results with maximum effect and minimal side effects. It is the general object of such therapeutic approaches to interfere with or otherwise modulate gene expression which would lead to undesired protein formation.

One method for inhibiting specific gene expression is the use of oligonucleotides as "antisense" agents. The oligonucleotides complementary to a specific, target, messenger RNA (mRNA) sequence are used. A number of workers have reported such attempts. Pertinent reviews include C. A. Stein & J. S. Cohen, *Cancer Research*, vol. 48, pp. 2659–2668 (1988); J. Walder, *Genes & Development*, vol. 2, pp. 502–504 (1988); C. J. Marcus-Sekura, *Anal. Biochemistry*, vol. 172, 289–295 (1988); G. Zon, *Journal of Protein Chemistry*, vol. 6, pp-131–145 (1987); G. Zon, *Pharmaceutical Research*, vol. 5, pp. 539–549 (1988); A. R. Van der Krol, J. N. Mol, & A. R. Stuitje, *BioTechniques,* vol. 6, pp. 958–973 (1988) and D. S. Loose-Mitchell, *TIPS,* vol. 9, pp. 45–47 (1988). Each of the foregoing provide background concerning general antisense theory and prior techniques.

Thus, antisense methodology has been directed to the complementary hybridization of relatively short oligonucleotides to single-stranded mRNA or single-stranded DNA such that the normal, essential functions of these intracellular nucleic acids are disrupted. Hybridization is the sequence specific hydrogen bonding of oligonucleotides via Watson-Crick base pairs to RNA or single-stranded DNA. The bases of such base pairs are said to be complementary to one another.

Prior attempts at antisense therapy have provided oligonucleotides which are designed to bind in a specific fashion to—i.e., which are specifically hybridizable with—a specific mRNA by hybridization. Such analogs are intended to inhibit the activity of the selected mRNA—i.e., to interfere with translation reactions by which proteins coded by the mRNA are produced—by any of a number of mechanisms. It has been hoped to provide therapeutic benefits by inhibiting the formation of the specific proteins which are coded for by the mRNA sequences.

A number of chemical modifications have been introduced into antisense oligonucleotides to increase their therapeutic activity. Such modifications are designed to increase cell penetration of the antisense oligonucleotides, to stabilize them from nucleases and other enzymes that degrade or interfere with the structure or activity of the oligonucleotides in the body, to enhance their binding to targeted RNA, to provide a mode of disruption (terminating event) once sequence-specifically bound to targeted RNA, and to improve their pharmacokinetic properties. At present, however, no generalized antisense oligonucleotide therapeutic or diagnostic scheme has been found. The most serious deficiency of prior efforts has been the complete lack of a termination event once appropriate hybridization takes place or the occurrence of a termination event that is so inefficient that a useful potency cannot be achieved due to the inability of oligonucleotides to be taken into cells at effective concentrations. The activity of the antisense oligonucleotides presently available has not been sufficient for effective therapeutic, research reagent, or diagnostic use in any practical sense. Accordingly, there has been and continues to be a long-felt need for oligonucleotides which are capable of effective therapeutic and diagnostic antisense use.

This long-felt need has not been satisfied by prior work in the field of antisense oligonucleotide therapy and diagnostics. Others have failed to provide materials which are, at once, therapeutically or diagnostically effective at reasonable rates of application.

Initially, only two mechanisms or terminating events have been thought to operate in the antisense approach to therapeutics. These are the hybridization arrest mechanism (i.e., arrest of translation via antisense hybridization) and the cleavage of hybridized RNA by the cellular enzyme, ribonuclease H (RNase H). It is likely that additional "natural" events may be involved in the disruption of targeted RNA, however. Other terminating events also have been studied in an attempt to increase the potency of oligonucleotides for use in antisense diagnostics and therapeutics. Thus, an area of research has developed in which a second domain of the oligonucleotide, generally referred to as a pendant group, has been introduced.

The pendant group is not involved with the specific Watson-Crick hybridization of the oligonucleotide with the mRNA but is carried along by the oligonucleotide to serve as a reactive functionality. The pendant group is intended to interact with the mRNA in some manner to more effectively inhibit translation of the mRNA into protein. Such pendant groups have also been attached to molecules targeted to either single or double stranded DNA.

The type of pendant group known as an intercalating agent has been disclosed by Cazenave, N. Loreau, N. T.

Thuong, J. J. Toulme and C. Helene in *Nucleic Acid Research*, vol. 15, pp. 4717–4736 (1987) and J. F. Constant, P. Laugaa, B. P. Roques & J. Lhomme, in *Biochemistry*, vol. 27, pp. 3997–4003 (1988). The disclosed purpose of such intercalating agents is to add binding stability to the hybrid formed between the oligonucleotide and the target nucleic acid by binding to the duplex formed between them.

It has also been disclosed to provide a pendant group to oligonucleotides which is capable of cross-linking. Thus, a pendant agent such as psoralen has been disclosed by A. T. Yeung, B. K. Jones and C. T. Chu in *Biochemistry*, vol. 27, pp. 2304–3210 (1988). It is believed that after hybridization of the oligonucleotide to the target mRNA, the psoralen is photoactivated to cross-link with the mRNA forming a covalent bond between the oligonucleotide and the mRNA, thereby permanently inactivating the mRNA molecule and precluding the further formation of protein encoded by that particular portion of RNA.

It has also been proposed to employ an alkylating agent as a pendant group for oligonucleotides for use in antisense approaches to diagnostics and therapeutics, as disclosed by R. B. Meyer in the *Journal of American Chemical Society*, Vol. 111, pp 8517–8519 (1989) and D. G. Knorre an V. V. Vlassov, *Progress in Nucleic Acid Research and Molecular Biology*, Vol.32, pp.291-320 (1985).

The object of employing alkylating agents as pendant groups in oligonucleotides in antisense approaches is to cause the alkylating agent to react irreversibly with the target mRNA. Such irreversible binding between the antisense oligonucleotide and the mRNA is generally covalent and leads to permanent inactivation of the mRNA with a concomitant halt in protein production from the portion of mRNA thus inactivated.

A further strategy which has been proposed is to use chemical reagents which, under selected conditions, can generate a radical species for reaction with the target nucleic acid to cause cleavage or otherwise to inactivate it. Proposed pendant groups of this category include coordination complexes containing a metal ion with associated ligands. A metal ion can change oxidation state to generate reactive oxygen-containing radical ions or other radical species. P. L. Doan, L. Perrouault, M. Chassignol, N. T. Thuong, & C. Helene, in *Nucleic Acids Research*, Vol. 15, pp. 8643-8659 (1987) have disclosed iron/EDTA and iron/porphyrin species for this purpose. Copper/phenanthroline complexes have been disclosed by D. S. Sigman, in Accounts of Chemical Research, Vol. 19, pp. 180-186 (1986). G. B. Dreyer and P. B. Dervan, in *Proceedings of the National Academy of Sciences, U.S.A.*, Vol. 82, pp.968-972 (1985) have investigated the EDTA/Fe moiety to cleave nucleic acids.

Prior approaches using cross-linking agents, alkylating agents, and radical-generating species as pendant groups on oligonucleotides for antisense diagnostics and therapeutics have several significant shortcomings. The sites of attachment of the pendant groups to oligonucleotides play an important, yet imperfectly known, part in the effectiveness of oligonucleotides for therapeutics and diagnostics. Prior workers have described most pendant groups as being attached to a phosphorus atom which, as noted above, affords oligonucleotides with inferior hybridization properties. Prior attempts have been relatively insensitive in that the reactive pendant groups have not been effectively delivered to sites on the messenger RNA molecules for alkylation or cleavage in an effective proportion. Moreover, even if the reactivity of such materials were perfect, i.e. if each reactive functionality were to actually react with a messenger RNA molecule, the effect would be no better than stoichiometric. That is, only one mRNA molecule would be inactivated for each molecule of oligonucleotide. It is also likely that the non-specific interactions of the modified oligonucleotides with molecules other than the target RNA, for example with other molecules that may be alkylated or which may react with radical species, as well as possible self-destruction of the oligonucleotides, not only diminishes the diagnostic or therapeutic effect of the antisense treatment but also leads to undesired toxic reactions in the cell or in vitro. This is especially acute with the radical species which are believed to be able to diffuse beyond the locus of the specific hybridization to cause undesired damage to non-target materials, other cellular molecules, and cellular metabolites. This perceived lack of specificity and stoichiometric limit to the efficacy of such prior alkylating agent and radical generating-types of antisense oligonucleotides is a significant drawback to their employment.

Accordingly, there remains a great need for antisense oligonucleotide formulations which are capable of improved specificity and effectiveness both in binding and in mRNA modulation or inactivation without the imposition of undesirable side effects.

OBJECTS OF THE INVENTION

It is one object of this invention to provide oligonucleotides for use in antisense oligonucleotide diagnostics.

A further object of this invention is to provide such oligonucleotides which are less likely to evoke undesired or toxic side reactions.

A further object is to provide research and diagnostic methods and materials for assaying bodily states in animals, especially diseased states.

A further object is to provide means for modifying nucleic acids for effecting substitutions on selective portions thereof.

Still another object is to provide means for the selective cleavage of RNA.

These and other objects will become apparent to persons of ordinary skill in the art from a review of the present specification and appended claims.

SUMMARY OF THE INVENTION

In accordance with the present invention, compositions for cleaving RNA are provided. These compositions comprise a targeting portion specifically hybridizable with a preselected portion of RNA. The compositions further comprise intercalating portions capable of intercalating between base pairs formed upon hybridization with RNA. The compositions further comprise a reactive portion capable of catalyzing, alkylating, or otherwise effecting the cleavage of RNA, especially of its phosphodiester bonds. Preferred compositions according to the present invention comprise at least one ribofuranosyl unit which bears at its 2' position both an intercalating portion and a reactive portion. The compositions may also include a tether or some other means for connecting the targeting and reactive portions together to form the composition.

The targeting portion of the compositions of this invention preferably comprises an oligonucleotide including from about 3 to about 50 base units with 8 to 40 subunits being preferred and 12 to 25 being still more preferred. Oligonucleotides having about 15 base units are preferable for the practice of certain embodiments of the present invention. Preferably, the targeting portion is an analog of an oligonucleotide wherein at least some of the phosphodiester bonds of the oligonucleotide have been substituted with a structure which functions to enhance nuclease resistance. It is preferred that such substitutions comprise phosphorothioate bonds or short chain alkyl or cycloalkyl structures. In accordance with other preferred embodiments, the phosphodiester bonds are substituted with structures which are, at once, substantially non-ionic and non-chiral.

In certain preferred embodiments, the intercalating portions of the compositions are known, non-carcinogenic types of polycyclic aromatic hydrocarbons or heterocyclic moieties capable of intercalating between predetermined base pairs formed by a hybrid.

In accordance with other preferred embodiments the reactive portion of the composition comprises a functionality capable of catalyzing the hydrolysis or cleavage of phosphodiester bonds in RNA. Such functionalities may either be basic, acidic, amphoteric, ionic, or hydrophobic. Heteroatomic species can be formulated to be either basic or acidic or, indeed, to be amphoteric for such purposes.

This invention also comprehends the employment of alkylating and free-radical-forming functionalities as the reactive portions of the subject compositions, particularly where said alkylating or free-radical-forming materials are delivered into the minor groove of the hybrid formed between the compositions of the invention and the RNA to be cleaved.

In accordance with other embodiments, the compositions of the invention for cleaving RNA comprise heterocyclic structures having at least one RNA cleaving moiety or some other moiety capable of interacting with an RNA appended thereto. Certain of these compositions are adapted for delivery of the RNA cleaving (i.e., intercalating or minor-groove-binding) moiety to a predetermined portion of the RNA strand, in part by carefully selecting the sites for attachment of the heterocyclic RNA cleaving moieties to the complementary oligonucleotide or analog. Compositions of the invention may include naturally occurring or non-naturally occurring sugar portions, as well as naturally occurring or non-naturally occurring base portions. Accordingly, novel nucleosides and nucleoside analogs are provided. Such nucleosides and nucleoside analogs may be incorporated into oligonucleotides which are useful in the practice of the invention.

The invention also is directed to methods for cleaving an RNA comprising contacting an organism having the RNA with a composition formulated in accordance with the foregoing considerations. It is preferred that the RNA which is to be modulated be preselected to comprise preferably messenger RNA. The invention may also be applied to pre-messenger RNA and, indeed, to RNA generically and to double-stranded DNA. The targeting portion of the composition to be employed is selected to be complementary to the preselected portion of RNA, that is, to be a complementary oligonucleotide for that portion.

The invention is also directed to the utilization of groups appended to oligonucleotides which do not include a reactive function. Such pendant groups may lead to enhanced oligonucleotide uptake, enhanced resistance of oligonucleotide to degradation by nucleases, and stronger binding of the oligonucleotides to targeted RNA.

The invention is also directed to functionalities which serve to attach reporter groups such as biotin and various fluorophores to sequence-specific oligonucleotides for diagnostic purposes. More than one non-reactive functionality may be attached to each oligonucleotide, two or more nonreactive functionalities may be attached to a single nucleoside unit, and a combination of non-reactive functionalities and reactive functionalities may be attached to a single nucleoside unit or a single oligonucleotide.

In accordance with other preferred embodiments of the present invention, compositions which are resistant to nuclease degradation are provided. These compositions are comprised of sugar-modified oligonucleotides, the targeting portions of which are specifically hybridizable with preselected nucleotide sequences of single-stranded or double-stranded DNA or RNA. The sugar-modified oligonucleotides recognize and form double strands with single-stranded DNA and RNA or triple strands (triplex structures) with double-stranded DNA and RNA.

The nuclease resistant oligonucleotides of this invention consist of a single strand of nucleic acid bases linked together through linking groups. The target portion of the nuclease resistant oligonucleotide may range in length from about 5 to about 50 nucleic acid bases. However, accordance with the preferred embodiment of this invention, a target sequence of about 15 bases in length is believed to be optimal.

The nucleic acid bases may be pyrimidines such as thymine, uracil or cytosine, or purines such as guanine or adenine, or both, arranged in a specific sequence. Additionally, they may be any of the novel bases of the invention. The sugar moiety of such bases may be of the deoxyribose or ribose type. The groups linking the bases together may a sugar-phosphate-nucleic acid backbone, but may also be modified linking groups such as, for example, phosphorothioate, methylphosphonate, or phosphate alkylated moieties.

The resulting novel oligonucleotides are resistant to nuclease degradation and exhibit hybridization properties of higher quality relative to wild type (DNA-DNA and RNA-DNA) duplex&s and the phosphorus modified oligonucleotide duplexes containing phosphorothioates, methylphosphonates, phophoramidates and phosphorotriesters.

The invention further is directed to diagnostic methods for detecting the presence or absence of abnormal RNA molecules or abnormal or inappropriate expression of normal RNA molecules in organisms or cells. It is also directed to methods for the selective cleaving of RNA such as for research and diagnostics and to the RNA thus formed. Such selective cleaving is accomplished by interacting RNA with compositions of the invention which have reactive portions capable of effecting such cleavage and targeting portions designed to enforce selectivity.

The compositions useful for effecting the cleavage of an RNA or detecting its presence in accordance with this invention generally comprise three portions. The first portion, the targeting portion, is a portion which is specifically hybridizable with a preselected nucleotide sequence of the RNA to be modulated. The targeting portion of the composition is an oligonucleotide. It is designed and prepared conveniently, through solid state synthesis of known methodology, to be complementary to or at least to be specifically hybridizable with the preselected nucleotide sequence of the RNA. Nucleic acid synthesizers are commercially available and their use is generally understood by persons of ordinary skill in the art to be capable of generating nearly any oligonucleotide of reasonable length which may be desired.

The invention further is directed to diagnostic methods for detecting the presence or absence of abnormal RNA molecules or abnormal or inappropriate expression of normal RNA molecules in organisms or cells.

The invention is also directed to methods for the selective binding of RNA for research and diagnostic purposes. Such selective, strong binding is accomplished by interacting such RNA or DNA with compositions of the invention which are resistant to degradative nucleases and may hybridize more strongly and with greater fidelity than any other known oligonucleotide.

In accordance with a further embodiment of the invention, novel processes are provided for the synthesis of novel nucleoside analogs that are substituted in the 2' position and which are useful for incorporation into oligonucleotides of the invention. Such process provides for introduction of a 2' substituent in the absence of blocking of either the 3' or 5' hydroxyl groups of a ribofuranosyl nucleoside. Such processes utilize treatment with sodium hydride followed by use of an alkyl halide or, for uracil, stannous chloride. No protecting groups on the nucleoside bases are necessary except for the exo-cyclic amino group of guanosine. The reactions are conducted at or near room temperature. These conditions are contrasted to prior known processes that require strong alkylating agents, for instance diazomethane. Such strong alkylating agents necessitate the complete protection of all reactive sites on the nucleoside bases and the 3' and 5' sugar hydroxyls.

Certain compositions useful for effecting the cleavage of an RNA molecule in accordance with this invention generally comprise a sugar modified oligonucleotide containing a targeting sequence which is specifically hybridizable with a preselected nucleotide sequence of single stranded or double stranded DNA or RNA molecule and which is nuclease resistant. The sequence is synthesized, typically through solid state synthesis of known methodology, to be complementary to or at least to be specifically hybridizable with the preselected nucleotide sequence of the RNA or DNA. Nucleic acid synthesizers are commercially available and their use is generally understood by persons of ordinary skill in the art as being effective in generating nearly any oligonucleotide of reasonable length which may be desired.

In the context of this invention, the term "oligonucleotide" in a first instance refers to a polynucleotide formed from a plurality of nucleotide units that are joined together via native internucleoside, phosphodiester linkages and that are formed from naturally-occurring bases and pentofuranosyl sugars groups. The term "oligonucleotide" thus includes naturally occurring species or synthetic species formed from naturally occurring nucleotide units.

The term "oligonucleotide" also includes polynucleotides formed from non-naturally occurring or modified subunits. These modifications can occur on the base portion of a nucleotide, on the sugar portion of a nucleotide or on the linkage joining one nucleotide to the next. In addition, modification can be made wherein nucleoside units are joined together with connecting groups that substitute for the inter-nucleoside phosphate linkages. Such linkages include an —O—CH$_2$—CH$_2$—O— linkage and other novel linkages as are disclosed in U.S. Pat. No. 5,223,618 and U.S. patent application Ser. No. 703,619, filed May 21, 1991, entitled Backbone Modified Oligonucleotide Analogs, both assigned to the assignee of this invention. Other modifications can be made to the sugar, to the base, or to the phosphate group of the nucleotide. Exemplary of such modification are those modification disclosed in U.S. patent applications Ser. No. 463,358, filed Jan. 11, 1990, entitled Compositions And Methods For Detecting And Modulating RNA Activity; Ser. No. 566,977, filed Aug. 13, 1990, entitled Sugar Modified Oligonucleotides That Detect And Modulate Gene Expression; U.S. Pat. No. 5,138,045, Ser. No. 558,806, filed Jul. 27, 1991, entitled Nuclease Resistant Pyrimidine Modified Oligonucleotides That Detect And Modulate Gene Expression and Ser. No. PCT/US91/00243, filed Jan. 11, 1991, entitled Compositions and Methods For Detecting And Modulating RNA Activity, all assigned to the assignee of this invention. The disclosures of all of the above noted patents are herein incorporated by reference Thus the terms oligonucleotide, as used in connection with this invention, in addition to natural units, also refers to structures that include modified portions, be they modified sugar moieties, modified base moieties or modified sugar linking moieties, that function similarly to natural bases, natural sugars and natural phosphodiester linkages. Exemplary among these are phosphorothioate, phosphorodithioate, methyl phosphonate, phosphotriester or phosphoramidate inter-nucleoside linkages used in place of phosphodiester inter-nucleoside linkages; deaza or aza purines and pyrimidines used in place of natural purine and pyrimidine bases; pyrimidine bases having substituent groups at the 5 or 6 position; purine bases having altered or replacement substituent groups at the 2, 6 or 8 positions; or sugars having substituent groups at their 2' position, substitutions for one or more of the hydrogen atoms of the sugar, or carbocyclic or acyclic sugar analogs. They may also comprise other modifications consistent with the spirit of this invention. Such oligonucleotides are best described as being functionally interchangeable with natural oligonucleotides (or synthesized oligonucleotides along natural lines), but which have one or more differences from natural structure. All such oligonucleotides are comprehended by this invention so long as they function effectively to mimic the structure of a desired RNA or DNA strand.

The targeting portions of the compositions of the present invention are preferably oligonucleotides having from about 3 to about 50 base units. It is more preferred that such oligonucleotides have from about 8 to about 40 base units and even more preferred that from about 12 to about 25 be employed. At present, it is believed that oligonucleotides having about 15 base units will likely be found to be best for the practice of certain embodiments of the present invention. It is desired that the targeting portion be adapted so as to be specifically hybridizable with the preselected nucleotide sequence of the RNA selected for cleavage.

At present, the oligonucleotides which are believed to be particularly suitable for the practice of one or more embodiments of the present invention will comprise one or more subunits having general structure (1).

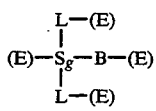

(1)

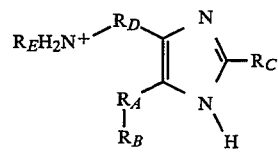

(2)

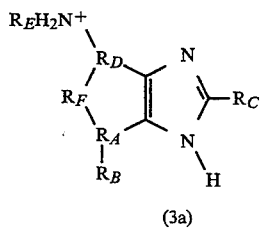 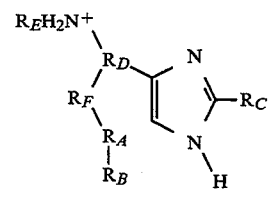

(3a) (3b)

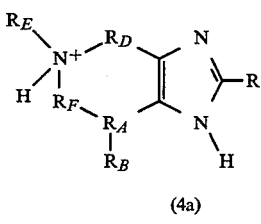 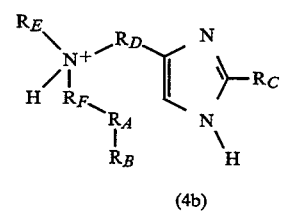

(4a) (4b)

wherein B is any of the purine or pyrimidine bases, including those which are known for naturally occurring and non-naturally occurring oligonucleotides or which exhibit similar functions; (E) is attached at one or more of the indicated positions and is a RNA cleaving moiety, H, OH, or other small base substituent groups; $S_g$ is a naturally-occurring or non-naturally occurring sugar; and L is a sugar-linking group. The sugar-linking group L may be any of those structures either naturally occurring, described herein, or otherwise known which are capable of linking sugar moieties of oligonucleotides or sugar analogs together to form the targeting portion of the compositions of this invention. It is preferred that these sugar-linking functions either comprise a phosphodiester structure or a substantially non-ionic, substantially non-chiral structure as described herein, such as lower alkyl and cycloalkyl, especially $C_2$–$C_4$ alkyl. Note that when lower alkyl structures are employed, the 5' methylenes of one or more sugars may be eliminated. Preferably, at least some of the phosphodiester bonds of said oligonucleotide are substituted with phosphorothioate, methyl phosphonate, or alkyl phosphate.

As will be appreciated by persons of ordinary skill in the art, variations in the structures of the sugar moieties useful in the preparation of the subject compositions may be made without deviating from the spirit of the invention. Once again, it is not necessary that every sugar-linking function be in a modified form. A substantial number and even a predominance of such linking groups may exist in the native, phosphodiester form as long as the overall targeting portion of the compositions of the molecules exhibits an effective ability to penetrate into the intracellular spaces of cells of the organism in question or otherwise to contact the target RNA and to specifically bind therewith to form a hybrid capable of detecting the RNA. Of course, fully unmodified, native phosphodiester structures may be used as well.

It is not necessary to tether more than one, or perhaps two RNA cleaving functionalities to the oligonucleotide in accordance with this invention in order to provide the benefits of the invention. Thus, an RNA cleaving moiety will preferably be tethered to a relatively small proportion of the subunits, generally only one or two, comprising the oligonucleotide which is the targeting portion of the compositions of the invention. In other embodiments of the invention, however, all of the nucleotides in an oligonucleotide can be modified to include one or more RNA cleaving moieties.

It is believed desirable in accordance with certain preferred embodiments to attach the RNA cleaving portion and the intercalating portion of the compositions of this invention to one of the nucleosides forming a subunit of the targeting portion. Such an attachment may be depicted in accordance with structures (2)–(4b):

wherein:

$R_A$ is H, aryl, substituted aryl, or nitrogen heterocyclic;

$R_B$ is $S_g$—2'—O—$(CH_2)_n$—O—, $S_g$—2'—O—$(CH_2)_n$—NH—, $S_g$—2'—O—$(CH_2)_n$—CH_2—, $S_g$—2'—O—$(CH_2CH=CH_2)_n$—, B—, or L—;

$R_C$ is H, O⁻, OH, COO⁻, OCH_3, NH_2, C($R_G$)($R_H$)($R_I$), N($R_G$)($R_H$)($R_I$), Cl, SCH_3, NHC(O)CH_3, OC(O)R_6, NO, nitrogen heterocyclic or another electron donating group;

$R_D$ is $(CH_2)_q$;

$R_E$ is H, $(CH_2)_n$—$R_J$, or a chemical functional group comprising $R_J$;

$R_F$ is H, $(CH_2)_n$, $(CH\alpha CHCH_2)_n$, aryl, or cycloalkyl;

$R_G$, $R_H$, and $R_I$ are, independently, H, alkyl, or substituted alkyl;

$R_J$ is H, nitrogen heterocyclic, a positively charged group, or a phosphoryl hydrogen bond donating group;

B is a purine or pyrimidine base or a derivative thereof;

L is a sugar-linking group;

$S_g$ is a naturally occurring or non-naturally occurring sugar;

n is from about 1 to about 5; and q is from about 1 to about 5.

$R_A$ preferably is selected to promote intercalation between the base pairs of the oligonucleotide/RNA target sequence heteroduplex. Along with the imidazole ring portion of structures (2)–(4b), it is believed to be a contributor to the net intercalative binding energy. Representative $R_A$ include phenyl, substituted phenyl, naphthyl, anthracenyl, 2,7-diaza-anthracenyl, pyrenyl, acridinyl, 9-aminoacridinyl, and pyridinyl moieties. $R_A$ preferably is a polycyclic aromatic hydrocarbon such as a naphthyl residue. Preferred polycyclic aromatic hydrocarbons are non-carcinogenic moieties which do not bind RNA or DNA with a strong sequence dependence.

According to the present invention, $R_B$ is a covalent linker joining $R_A$ to a sugar moiety, to a base moiety, or to an alkyl or alkoxy sugar-linking moiety. In preferred embodiments, $R_B$ is $S_g$—2—O—CH$_2$—CH$_2$—.

$R_C$ preferably is electron donating, through inductive and/or resonance effects. It is believed that $R_C$ serves to upwardly adjust the pK$_a$ of the imidazole residue in structures (2)-(4b). In a steric sense, $R_C$ is intended to lie in the RNA minor groove without affecting RNA hybridization or intercalative binding via $R_A$ and/or the imidazole residue. $R_C$ may be designed to contain a proton-accepting group to assist deprotonation of the 2' hydroxyl of a target RNA.

$R_D$ preferably is a covalent linker joining the 5-position of the imidazole residue and the amine function, $H_2R_EN^+$. $R_D$ preferably comprises about 1-5 carbon atoms. As will be recognized, the existence of the amine function in either protonated or neutral form is media dependent. The amine function is intended to lie in the RNA major groove and to complex with the RNA internucleotide phosphate diester through electrostatic and/or hydrogen bonding to RNA phosphate oxygens. Such complexation is intended to properly orient RNA cleaving moieties such as the imidazole residue and to directly enhance the rate of cleavage. Such rate enhancement is believed to be effected through polarization and weakening of RNA phosphorus-oxygen bonds, making the phosphorus atom more electrophilic and more reactive to attack by a 2'-oxygen atom. The amine function is also believed to stabilize the resulting transition states and intermediates, making the phosphate oxygens better proton acceptors.

In preferred embodiments, $R_E$ comprises an alkyl chain of up to about 3 carbon atoms and a further moiety known to assist RNA cleaving, $R_J$. Preferably, $R_J$ is a nitrogen heterocycle, more preferably an imidazole. This function is intended to pre-protonate one of the two non-sugar linked phosphate oxygens in an initial chemical step to make the phosphorus more electrophilic and reactive to attack by a 2' oxygen anion, $O^-$. It is particularly preferred that $R_J$ have one of the structures:

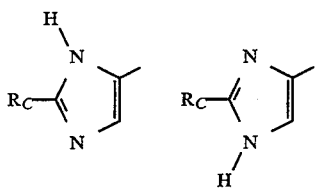

where $R_C$ is as defined above or is a group that can hydrogen bond with or electrostatically interact with phosphate oxygens.

$R_F$ is a conformation-restricting moiety of variable size linking $R_A$ and the amine function. It can be mono- or polycyclic and/or acyclic, as well as saturated and-/or unsaturated. $R_F$ preferably is (CH$_2$)$_n$ where n is 1-3.

Two representative imidazole-based, RNA-cleaving oligonucleotides according to the present invention are depicted by structures (11) and (12), wherein DMT is dimethoxytrityl, CEO is cyanoethoxy, and Bz is benzyl. The latter are protective blocking groups of synthesis.

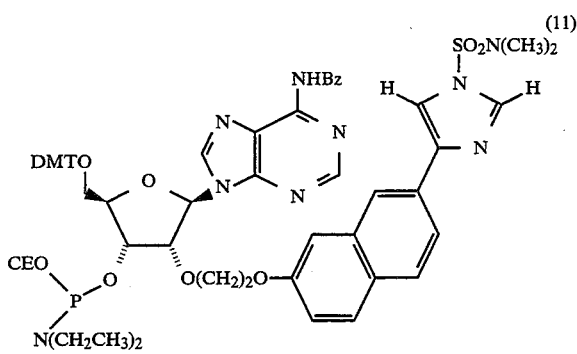

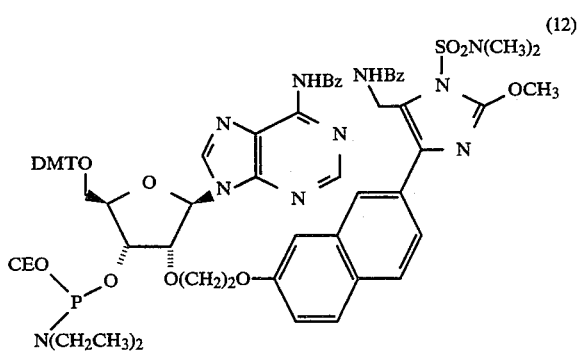

While not intending to be limited to any particular theory of the invention, it is believed that when the oligonucleotides of the present invention hybridize with RNA, the $R_A$ and, to a lesser extent, imidazole subunits appended to the 2' positions thereof intercalate with the RNA and thereby are constrained by the hybrid duplex to a fairly limited number of positions and conformations in comparison to designs lacking the intercalative moiety. By constraining the intercalative cleaver with the duplex in this manner, the specific RNA cleaving functionality is positioned for optimal delivery to hybridized RNA. It should be noted that limited local motion and positioning via the intercalative mode are allowed, such that the positively charged amine of structures (2)-(4b) may optimally fine-tune the orientation of the entire composition by hydrogen bonding and electrostatic interactions with the phosphate groups while retaining an intercalative binding mode. Accordingly, it is intended that the present invention include as a preferred embodiment all compositions comprising a ribofuranosyl nucleotide which bears at its 2' position substituents capable of both intercalating and cleaving RNA. The same substituents capable of both intercalating and cleaving RNA also may be functionalized via a suitable linker to any of the bases or to the oligonucleotide backbone.

It will be recognized that the structures (2)-(4b) can be coupled with the sugar portion of a given nucleoside at a variety of positions including, but not limited to, the 2' hydroxyl group as shown, for example, in structures (13) and (14):

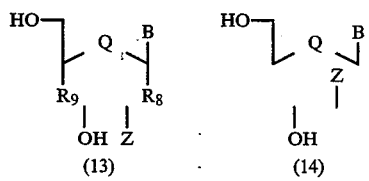

wherein:

Q is O or CR$_{11}$;

R$_8$ and R$_9$ are H, lower alkyl, substituted lower alkyl, an RNA cleaving moiety;

R$_{10}$ is H, lower alkyl, substituted lower alkyl, an RNA cleaving moiety;

B is a nucleoside base or blocked nucleoside base moiety; and

Z is one of structures (2)–(4b).

Alkyl groups of the invention include but are not limited to C$_1$–C$_{12}$ straight and branched chained alkyls such as methyl, ethyl, propyl, butyl, pentyl, hexyl, heptyl, octyl, nonyl, decyl, undecyl, dodecyl, isopropyl, 2-butyl, isobutyl, 2-methylbutyl, isopentyl, 2-methylpentyl, 3-methylpentyl, 2-ethylhexyl, 2-propylpentyl. Alkenyl groups include but are not limited to unsaturated moieties derived from the above alkyl groups including but not limited to vinyl, allyl, crotyl, propargyl. Aryl groups include but are not limited to phenyl, tolyl, benzyl, naphthyl, anthracyl, phenanthryl, pyrenyl, and xylyl. Halogens include fluorine, chlorine and bromine. Suitable heterocyclic groups include but are not limited to imidazole, tetrazole, triazole, pyrrolidine, piperidine, piperazine and morpholine. Amines include amines of all of the above alkyl, alkenyl and aryl groups including primary and secondary amines and "masked amines" such as phthalimide. Amines are also meant to include polyalkylamino compounds and aminoalkylamines such as aminopropylamine and further heterocyclo-alkylamines such as imidazol-1, 2 or 4-yl-propylamine. Substituent groups for the above include but are not limited to other alkyl, haloalkyl, alkenyl, alkoxy, thioalkoxy, haloalkoxy and aryl groups as well as halogen, hydroxyl, amino, azido, carboxy, cyano, nitro, mercapto, sulfides, sulfones and sulfoxides. Other suitable substituent groups also include rhodamines, coumarins, acridones, pyrenes, stilbenes, oxazolo-pyridocarbazoles, anthraquinones, phenanthridines, phenazines, azidobenzenes, psoralens, porphyrins and cholesterols.

The nucleosidic sites to which functionality may be attached, and the design of any intervening linker group, are critical to the design of compositions for sequence-specific destruction or modulation of targeted RNA. The functionality must not interfere with Watson-Crick base pair hydrogen bonding rules, as this is the sequence-specific recognition/binding factor essential for selection of the RNA to be cleaved. The nucleosidic sites of functionalization also must not preclude optimal placement of the functionalized composition to best fulfill structural and functional goals.

Approaches to perfect complementation between the modified oligonucleotides and targeted RNA will result in the most stable heteroduplexes. This is desired because the heteroduplex must have a half-life sufficient to allow the reactive or non-reactive functionalities of this invention to initiate RNA cleavage or disruption of RNA function.

The half life of the perfectly formed duplex will be greatly affected by the positioning of the tethered functional group. Inappropriate positioning of functional groups, such as placement on the Watson/Crick base pair sites, would preclude duplex formation. Other attachment sites may allow sequence-specific binding but may be of such low stability that the reactive functionality will not have sufficient time to initiate RNA cleavage.

For RNA cleavage, a further important factor concerning the placement of the tethered functionality is that it must have optimized molecular recognition with the receptive substrate located in the targeted RNA, for example of a general base group with the 2'-hydroxyl group. A variety of structural studies such as X-ray diffraction, chemical reaction, and molecular modeling may aid in this placement.

It has now been found that certain positions on the nucleosides of double-stranded nucleic acids are exposed in the minor groove and may be substituted without affecting Watson-Crick base-pairing or duplex stability. Reactive or non-reactive functionalities attached to these positions in accordance with this invention may initiate cleavage and destruction of targeted RNA or interfere with its activity.

Reactive functionalities or pendant groups of oligonucleotides previously described in the literature have been almost exclusively placed on a phosphorus atom, the 5-position of thymine, or the 7-position of purines. A phosphorus atom attachment site can allow a reactive group to access both the major and minor grooves or to intercalate between base pairs. However, internal phosphorus modification can result in greatly reduced heteroduplex stability except with intercalator placement. Attachments at the 3' and/or 5' ends are limiting in that only one or two functional groups can be accommodated in the oligonucleotide. Even successful cleavage will not drive turnover. Functionality placed in the 5-position or 7-position of heterocycles (bases) pyrimidine and purine respectively will reside in the major groove of the duplex and will not be in proximity to the RNA 2'-hydroxyl substrate. However, such functional placement may be used to link to an intercalator bound between base pairs. Further, such placement can interfere with Watson-Crick binding.

It is possible that other positions for attachment of the RNA cleaving moieties having a similar effect may be found, especially when further modification of the purine or pyrimidine structure is undertaken or when backbone analogs suitable for functionalization are found, as may be done by persons of ordinary skill in the art without deviating from the spirit of the present invention. Once again, it will be understood that preferably one or at most a few RNA cleaving moieties generally should be employed. Thus, artisans in the field will have great latitude in selecting means of attachment of the RNA cleaving moieties in accordance with this invention.

The RNA cleaving moieties of the compositions of the present invention are designed in such a fashion that they can be effective in performing their proximate task, leading to the desired cleavage of RNA. It is believed to be useful to employ heteroatomic substitutions in the RNA cleaving moieties of these molecules, especially amides and polyamides, and indeed some may be preferred in order to ensure even tighter binding between the target mRNA and the compositions of the invention.

The nucleosides of the invention are linked together and to the rest of the oligonucleotide through a sugar-linking group. The linking group may be any of those structures described herein that are capable of linking sugar moieties of oligonucleotides together to form the targeting portion of the compositions of this invention. It is preferred that these sugar-linking groups comprise the phosphodiester structure or a derivative of such. Derivatives of the phosphodiester structure may include substitution of a sulphur, methyl, methyl oxide, or amine group for an oxygen. The sugar phosphate nucleic acid backbone may be modified as a phosphorothioate, methylphosphonate, or phosphate alkylated moiety. The phosphodiester linkage may also be replaced by a carbon or ether linkage as discussed above.

Without desiring to be bound by any particular theory of operation, it is believed that the reactive RNA cleaving functionalities described in this invention work by mechanisms involving any or all of:

1. phosphodiester bond cleavage via general acid/base catalysis with or without assistance via H-bonding, electrostatic interactions;
2. backbone sugar cleavage;
3. base alkylation cleavage; or
4. sugar alkylation, i.e., 2'-hydroxyl cross-linking.

One important aspect of this invention is the position and orientation of an appropriate reactive functionality of the targeting portion of this invention and the target RNA.

Phosphodiester bond cleavage can be accomplished by strategically positioning either proton-accepting, protondonating, or electron-accepting functional groups, represented by X, Y, and Z respectively, adjacent to such phosphodiester bonds, as shown in Scheme 1, wherein $B_1$ and $B_2$ are nucleoside base units. Additional placement of a proton-donating group, W-H, adjacent to one of the non-ester linkage phosphoryl oxygens may provide additional enhancement of cleavage.

Scheme 1

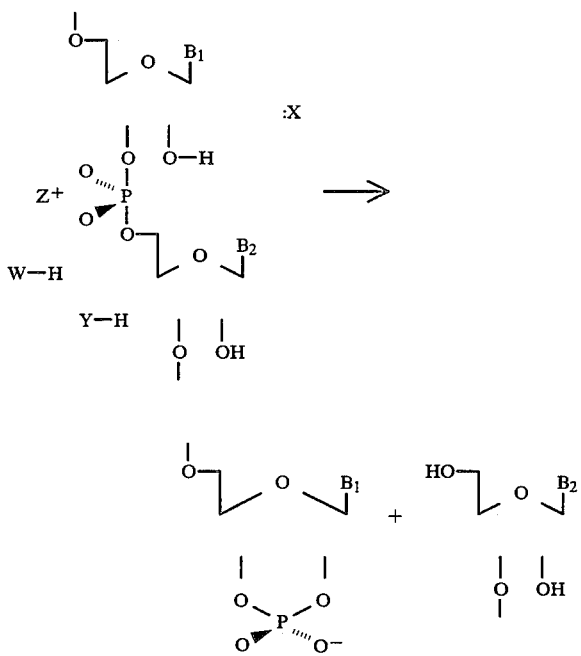

In some applications, one of the chemical groups may be sufficient to catalyze RNA cleavage. However, in other applications of the invention, the combination of two or even three groups may be preferred. Artisans in the field will have great latitude in selecting the specific reactive functionalities W, X, Y, and/or Z. There is also great latitude in the election to use one or more reactive functionalities in the same molecule.

The present novel approach to obtaining stronger binding and better molecular recognition of cleavage groups with target reactive groups is to prepare RNA mimics to bind to the targeted RNA. Therefore, a structure-activity relationship approach is undertaken to discover nuclease resistant oligonucleotides that maintain appropriate hybridization properties.

A series of 2'-modified nucleosides of adenine, guanine, cytosine, thymidine and certain analogs of these bases are prepared and are inserted as the modified nucleosides into sequence-specific oligonucleotides via solid phase nucleic acid synthesis. The novel oligonucleotides are assayed for their ability to resist degradation by nucleases and to possess hybridization properties comparable to the unmodified parent oligonucleotide. Initially, small electronegative groups are selected because these types are not likely to sterically interfere with required Watson-Crick base pair hydrogen bonding (hybridization). However, electronic changes due to the electronegativity of the atom or group in the 2'-position may profoundly effect the sugar conformation.

The oligonucleotides of this invention can be used in diagnostics and as research reagents and kits. The following procedures and examples illustrate the practice of this invention. These procedures and examples are not to be construed as limiting the invention.

Once nucleotides of the invention have been prepared, they can then subsequently be incorporated into oligonucleotides of the invention, which are synthesized by a standard solid phase, automated nucleic acid synthesizer such as the Applied Biosystems, Incorporated 380B or MilliGen/Biosearch 7500 or 8800. Triester, phosphoramidite, or hydrogen phosphonate coupling chemistries, M. Caruthers, Oligonucleotides. Antisense Inhibitors of Gene Expression., pp. 7–24, J. S. Cohen, ed. (CRC Press, Inc. Boca Raton, Fla., 1989), are used with these synthesizers to provide the desired oligonucleotides. The Beaucage reagent, Journal of American Chemical Society, Vol. 112, pp. 1253–1255 (1990) or elemental sulfur, S. Beaucage et al., Tetrahedron Letters, Vol. 22, pp. 1859–1862 (1981), is used with phosphoramidite or hydrogen phosphonate chemistries to provide substituted phosphorothioate oligonucleotides.

In preparing certain of the compounds of the invention fugitive masking groups are used. Such masking groups allow for ease of synthesis of the compounds. The masking groups are subsequently converted to the desired functionality. Such conversion preferably occurs during a standard deblocking step for a later reaction. An example of use of this procedure is the use of a phthalimide group for the introduction of an amino functionality. Alkyl phthalimides are attached at the proper position in a compound of interest, as for example a nucleoside, via a suitable intermediate such as an N-(haloalkyl)phthalimide. Upon completion of the synthesis of the compound of interest it is then used as a structural nucleotide for oligonucleotide synthesis utilizing standard oligonucleotide synthetic techniques on a nucleotide synthesizer. After the desired oligonucleotide is completed, it is cleaved from the synthesizer support and in doing so the cleaving reagent also converts the alkylphthalimide to the desired alkylamine. The above procedure can be expanded to attach longer chain polyamino functionalities to the oligonucleotides of the invention. Nucleotides or oligonucleotides having a first alkylamino functionality are treated with a further N-(haloalkyl) phthalimide. The extended functionality is then treated to yield the terminal amine group. This can be repeated to further extend the polyamino functionality as desired. Alternately, the extended polyamino functionality is first synthesized and reacted with the first alkylamino functionality to form the polyamino functionality.

EXAMPLE 1

Synthesis of 5'-(4,4'-Dimethoxytrityl)-3'-cyanoethoxydiethylphosphoamidityl)-2'—O—{3-propoxy-[2-naphthyl-7-(1-(dimethylaminosulfonyl)-imidazol-4-yl))]}-N6-benzoyl-adenosine (Structure 11)

1a. 2-Benzyl-7-trifluorosulfonylnaphthalene 2,7-dihydroxynaphthalene (Aldrich Chemical Co., Milwaukee, Wis.) in acetone was benzylated with benzylbromide in the presence of potassium carbonate to provide the monobenzylated product. This material was converted to the trifluoromethylsulfonyl derivative (triflate) with trifluoromethyl sulfonic acid anhydride and pyridine to yield the target compound.

1b. 1-(Dimethylaminosulfonyl)-2-(t-butyldimethyl silyl)-4-(tri-n-butyltin)-imidazole Imidazole was treated with dimethyl amino sulfonyl chloride providing 1-(dimethylaminosulfonyl)-imidazole, which was subsequently treated with n-butyl lithium and t-butyldimethylsilyl chloride to afford 1-(dimethylaminosulfonyl)-2-(t-butyldimethylsilyl)-imidazol e. This material was treated with n-butyllithium and tri-n-butyltin chloride to afford the target compound.

1c. 2-Benzyloxy-7-[(1-(dimethylaminosulfonyl)-imidazol-4-yl]-naphthalene

1-Hydroxy-7-[(1-dimethylaminosulfonyl)imidazol-4-yl]-naphthalene and 2-benzyl-7-trifluorosulfonylnaphthalene are reacted in the presence of palladium(O) and lithium chloride to provide the naphthalene and imidazole adduct, which is treated with hydrogen and palladium on charcoal to provide the target compound.

1d. 2-(1-Iodopropyl)-7-[(1-(dimethylamino sulfonyl)-imidazol-4-yl]-naphthalene

2-Hydroxy-7-[(1-(dimethylaminosulfonyl)-imidazol-4-yl]-naphthalene is reacted with 1,3-diodopropane to provide the target compound.

1e. 2'—O—{3-Propoxy-[2-naphthyl-7-(1-(dimethylamino-sulfonyl)-imidazol-4-yl)]}-N6-benzoyladenosine A mixture of N6-benzoyl-adenosine and 2-(1-iodopropyl)-7-[(1-(dimethylamino-sulfonyl)-imidazol-4yl]-naphthalene is reacted in DMF in the presence of sodium hydride to form the target compound.

EXAMPLE 2

Synthesis of 5'-(4,4'-Dimethoxytrityl)-3'-cyanoethoxydiethylphosphoamidityl)-2'—O—{3-propoxy-[2-naphthyl-7-(1-(dimethylaminosulfonyl-2-methoxy-5-acetylaminomethyl)-imidazol-4-yl))]}-n6-benzoyl-adenosine (Structure 12)

2a. 2-Hydroxy-7-[(1-dimethylaminosulfonyl-2-methoxy-4-benzoylaminomethyl-imidazol-4-yl)]-naphthalene 2-Benzyl-7-trifluoro methylsulfonyl-naphthalene is coupled with 1-dimethylaminosulfonyl-2-methoxy-4-cyano-5-iodoimidazole in the presence of palladium(O) and lithium chloride to provide the naphthalene and imidazole adduct. The cyano group is then reduced and the benzyl group removed with sodium in liquid ammonia. The aminomethyl group is then protected with a benzoyl group to provide the target compound.

2b. 2-(1-Iodopropoxy)-7-[(1-dimethylamino sulfonyl-2-methoxy-4-benzoylaminomethylimidazol-4-yl)]-naphthalene 2-Hydroxy-7-[(1-dimethylaminosulfonyl-2-methoxy-4-benzoylaminomethyl-imidazol-4-yl)]-naphthalene is reacted with 1,3-diodopropane in the presence of base to provide the target compound.

2c. 2'—O—{3-Propoxy-[2-naphthyl-7-(1-dimethylamino- sulfonyl-2-methoxy-4-benzoylaminomethyl)-imidazol-4-yl)]}-N6-benzoyl-adenosine A mixture of N6-benzoyl-adenosine and 2-(1-iodopropoxy)-7-[(1-dimethylaminosulfonyl-2-methoxy-4-benzoyl-aminomethyl-imidazol-4-yl)]-naphthalene is reacted in DMF in the presence of sodium hydride to form the title compound.

Oligonucleotides according to the present invention possessing intercalating RNA cleavers are prepared by inserting, via standard phosphoamidite coupling chemistry (Gait, M. J. (ed.) *Oligonucleotide Synthesis: A Practical Approach* 1984, IRL Press Ltd., Oxford, UK), one or more nucleosides modified with an intercalator-substituted imidazole adduct into an oligonucleotide sequence. Automated nucleic acid synthesizers such as the Applied Biosystems, Inc. 380B can be used to provide the desired modified oligonucleotides, followed by purification trityl-on reverse phase HPLC.

The length and the nature of the coupler between the 2'-position of the sugar and the 2-position of the substituted naphthalene can be adjusted by employing a variety of available chemistries. The imidazole can be substituted at its 1-, 2-, and 4-positions to adjust the $pK_a$, hydrogen bonding, and nucleophilicity of the resultant compound. The naphthalene-imidazole adduct can be placed on any nucleic acid nucleoside.

EXAMPLE 3

Hybridization Analysis

A. Evaluation of the Thermodynamics of Hybridization of Modified Oligonucleotides The ability of the functionalized oligonucleotides of the invention to hybridize to their complementary RNA or DNA sequences is determined by thermal melting analysis. The RNA complement is synthesized from T7 RNA polymerase and a template-promoter of DNA synthesized with an Applied Biosystems, Inc. 380B nucleic acid synthesizer. The RNA species is purified by ion exchange using FPLC (LKB Pharmacia, Inc.) or by denaturing urea-PAGE. Natural complementary oligonucleotides or those containing functionalization at specific locations are added to either the RNA or DNA complement at stoichiometric concentrations to form hybrid duplexes. The absorbance (260 nm) hyperchromicity dependence on temperature upon duplex to random coil transition is monitored using a Gilford Response II spectrophotometer. These measurements are performed in a buffer of 10 mM Na-phosphate, pH 7.4, 0.1 mM EDTA, and NaCl to yield an ionic strength of either 0.1M or 1.0M. Data are analyzed by a graphic representation of $1/T_m$ vs $\ln[Ct]$, where [Ct] is the total oligonucleotide concentration. From this analysis the thermodynamic parameters are determined. Based upon the information gained concerning the stability of the duplex or hetero-duplex formed, the placement of modified pyrimidine into oligonucleotides is assessed for its effects on helix stability. Modifications that drastically alter the stability of the hybrid exhibit reductions or enhancements in the free energy (delta G) and decisions concerning their usefulness in complementary oligonucleotides are made.

B. Fidelity of Hybridization of Modified Oligonucleotides

The ability of the modified oligonucleotides of the invention to hybridize with absolute specificity to the targeted mRNA is shown either by thermodynamic analysis (as above) with target sequences of varying sequence or by Northern blot analysis of purified target mRNA in the presence of total cellular RNA. Target mRNA is synthesized from a vector containing the cDNA for the target mRNA located downstream from a T7 RNA polymerase promoter. Synthesized mRNA is electrophoresed in an agarose gel and transferred to a suitable support membrane (i.e. nitrocellulose). The support membrane is blocked and probed using [$^{32}$P]-labeled antisense oligonucleotides. The stringency is determined by replicate blots and washing in either elevated temperatures or decreased ionic strength of the wash buffer. Autoradiography is performed to assess the presence of heteroduplex formation and the autoradiogram quantitated by laser densitometry (LKB Pharmacia, Inc.) or phosphorimaging (Molecular Dynamics, Inc.). Stringency is predetermined for the unmodified oligonucleotides and the conditions used such that only the specifically targeted mRNA is capable of forming a heteroduplex with the 2'-modified oligonucleotide.

EXAMPLE 4

Nuclease Resistance

A. Evaluation of the Resistance of Modified Oligonucleotides to Serum and Cytoplasmic Nucleuses Natural phosphorothioate and modified oligonucleotides of the invention are assessed for their resistance to serum nucleases by incubation of the oligonucleotides in media containing various concentrations of fetal calf serum or adult human serum. Labeled oligonucleotides are incubated for various times, treated with protease K and then analyzed by gel electrophoresis on 20% polyacrylamide-urea denaturing gels and subsequent autoradiography or phosphor-imaging. Autoradiograms are quantitated by laser densitometry. Based upon the location of the modifications and the known length of the oligonucleotide it is possible to determine the effect of the particular modification on nuclease degradation. For the cytoplasmic nucleases, a HL60 cell line is used. A post-mitochondrial supernatant is prepared by differential centrifugation and the labeled oligonucleotides are incubated in this supernatant for various times. Following the incubation, oligonucleotides are assessed for degradation as outlined above for serum nucleolytic degradation. Autoradiography results are quantitated for comparison of the unmodified—i.e., phosphorothioate—and the modified oligonucleotides.

B. Evaluation of the Resistance of Modified Oligonucleotides to Specific Endo- and Exo-Nucleases Evaluation of the resistance of natural and 2'-modified oligonucleotides to specific nucleases (i.e., endonucleases, 3',5'-exo-, and 5',3'-exonucleases) is performed to determine the exact effect of the modifications on degradation. Modified oligonucleotides are incubated in defined reaction buffers specific for various selected nucleases. Following treatment of the products with proteinase K, urea is added and analysis on 20% polyacrylamide gels containing urea is done. Gel products are visualized by staining using Stains All (Sigma Chemical Co.) Laser densitometry is used to quantitate the extent of degradation. The effects of the modifications are determined for specific nucleases and compared with the results obtained from the serum and cytoplasmic systems.

What is claimed is:

1. A compound having the structure:

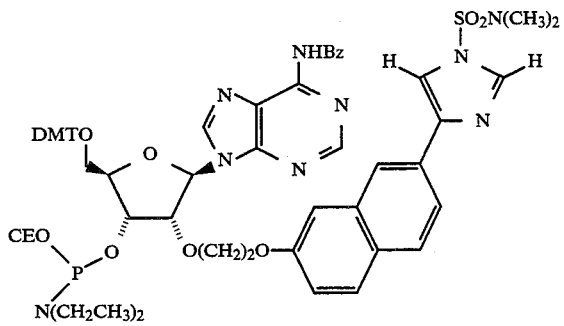

wherein DMT is dimethoxytrityl, CEO is cyanoethoxy, and Bz is benzyl.

2. A compound having the structure:

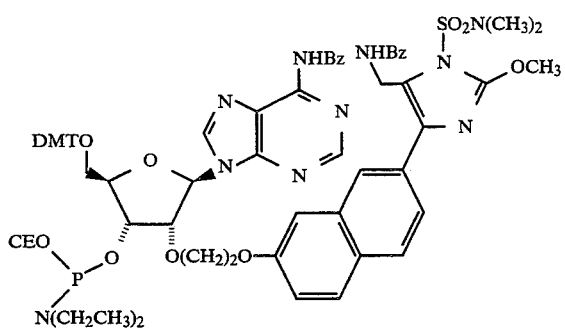

wherein DMT is dimethoxytrityl, CEO is cyanoethoxy, and Bz is benzyl.

* * * * *

UNITED STATES PATENT AND TRADEMARK OFFICE
CERTIFICATE OF CORRECTION

PATENT NO. : 5,359,051
DATED : October 25, 1994
INVENTOR(S) : Phillip D. Cook et al It is certified that error appears in the above-indentified patent and that said Letters Patent is hereby corrected as shown below:

Col. 8, line 24, after "reference" the period --.-- is missing.

Col. 10, line 42," ($CH\alpha CHCH_2$) should be --$CH=CHCH_2$)n--.

Col. 11, line 2, the equation "$R_B$ is $S_g$-2-O-$CH_2$-$CH_2$-." should be --$R_B$ is $S_g$- 2'-O-$CH_2$-$CH_2$-.--

Signed and Sealed this

Twenty-sixth Day of August, 1997

Attest:

BRUCE LEHMAN

Attesting Officer

Commissioner of Patents and Trademarks